(12) United States Patent
Saito et al.

(10) Patent No.: US 10,578,564 B2
(45) Date of Patent: Mar. 3, 2020

(54) METHOD FOR PRODUCING SILVER NANOWIRES, SILVER NANOWIRES, AND INK USING SAME

(71) Applicant: DOWA HOLDINGS CO., LTD., Tokyo (JP)

(72) Inventors: Hirotoshi Saito, Tokyo (JP); Daisuke Kodama, Tokyo (JP); Kimitaka Sato, Tokyo (JP)

(73) Assignee: DOWA HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 16/249,023

(22) Filed: Jan. 16, 2019

(65) Prior Publication Data

US 2019/0154598 A1   May 23, 2019

Related U.S. Application Data

(62) Division of application No. 15/122,200, filed as application No. PCT/JP2015/056162 on Mar. 3, 2015, now Pat. No. 10,220,441.

(30) Foreign Application Priority Data

Mar. 7, 2014   (JP) ................. 2014-045754

(51) Int. Cl.
  *H01B 1/02*   (2006.01)
  *G01N 23/046*   (2018.01)
  (Continued)

(52) U.S. Cl.
  CPC ............ *G01N 23/046* (2013.01); *B82Y 40/00* (2013.01); *C09D 11/52* (2013.01); *H01M 6/5083* (2013.01);
  (Continued)

(58) Field of Classification Search
  CPC .......... G01N 23/046; G01N 2223/419; G01N 2223/639; B82Y 40/00; H01L 21/02603; H01M 6/5083; H01M 10/4285; H01B 1/02
  (Continued)

(56) References Cited

U.S. PATENT DOCUMENTS

2005/0056118 A1   3/2005 Xia et al.
2008/0003130 A1   1/2008 Xia et al.
(Continued)

FOREIGN PATENT DOCUMENTS

JP   2010-084173   4/2010
JP   2013-503260   1/2013
(Continued)

OTHER PUBLICATIONS

C. Ducamp-Sanguesa et al., "Synthesis and . . . Uniform Shape", Journal of Solid State Chemistry 100, 272-280 (1992)/.

*Primary Examiner* — William D Young
(74) *Attorney, Agent, or Firm* — Clark & Brody

(57) ABSTRACT

A method for producing silver nanowires, containing reduction-precipitating silver in the form of wire in an alcohol solvent having dissolved therein a silver compound, the deposition being performed in the alcohol solvent having dissolved therein a chloride, a bromide, an alkali metal hydroxide, an aluminum salt, and an organic protective agent, the molar ratio Al/OH of the total Al amount of the aluminum salt dissolved in the solvent and the total hydroxide ion amount of the alkali metal hydroxide dissolved therein being from 0.01 to 0.40, the molar ratio OH/Ag of the total hydroxide ion amount of the alkali metal hydroxide dissolved in the solvent and the total Ag amount of the silver compound dissolved therein being from 0.005 to 0.50.

12 Claims, 5 Drawing Sheets

Example 1

(51) Int. Cl.
   *H01M 10/42* (2006.01)
   *H01M 6/50* (2006.01)
   *C09D 11/52* (2014.01)
   *B82Y 40/00* (2011.01)
   *B82Y 30/00* (2011.01)

(52) U.S. Cl.
   CPC ......... *H01M 10/4285* (2013.01); *B82Y 30/00* (2013.01); *G01N 2223/419* (2013.01); *G01N 2223/639* (2013.01); *H01B 1/02* (2013.01)

(58) Field of Classification Search
   USPC ....................................................... 252/500
   See application file for complete search history.

(56) References Cited

U.S. PATENT DOCUMENTS

| | | |
|---|---|---|
| 2009/0196788 A1 | 8/2009 | Wang |
| 2010/0078197 A1* | 4/2010 | Miyagishima ........ B22F 1/0025 174/128.1 |
| 2012/0000845 A1 | 1/2012 | Park |

FOREIGN PATENT DOCUMENTS

| | | |
|---|---|---|
| JP | 2013-531133 | 8/2013 |
| JP | 2014-505963 | 3/2014 |

\* cited by examiner

[Fig.1] Example 1
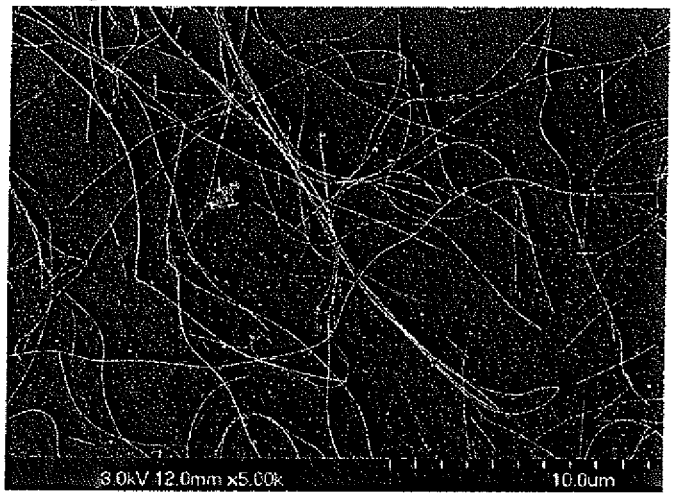
[Fig.2] Example 2
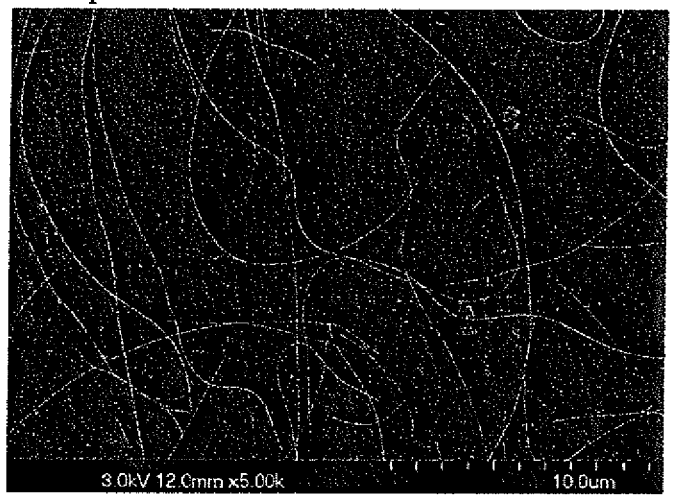
[Fig.3] Example 3

[Fig.4] Example 4
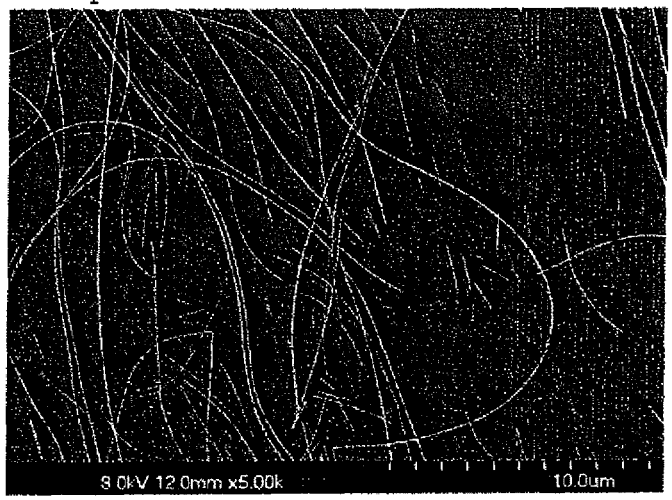
[Fig.5] Example 5
[Fig.6] Example 6

[Fig.7] Example 7
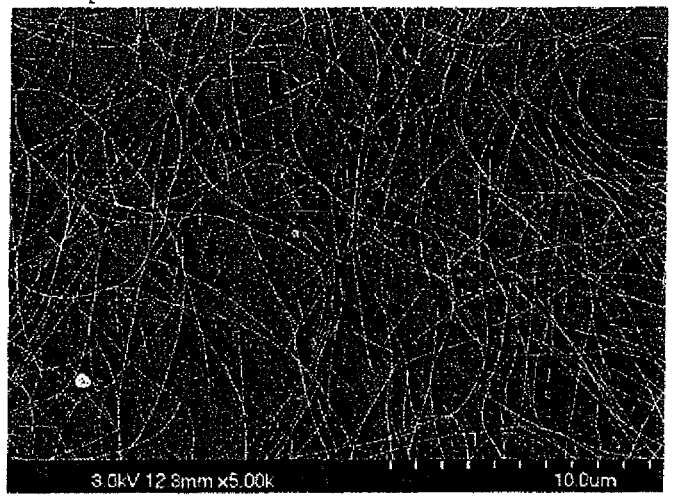
[Fig.8] Example 8
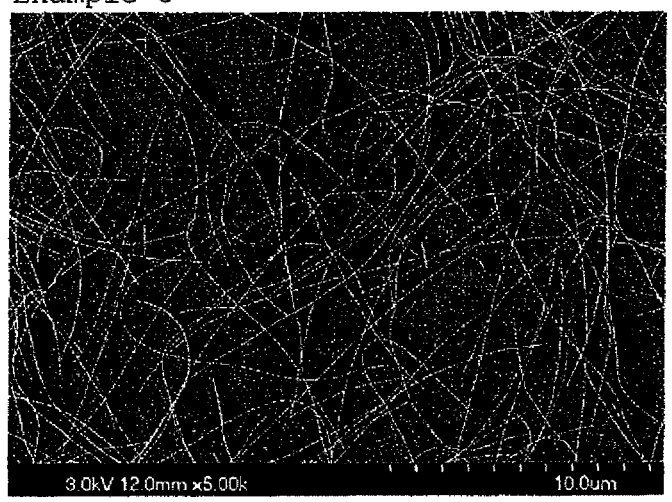
[Fig.9] Example 9
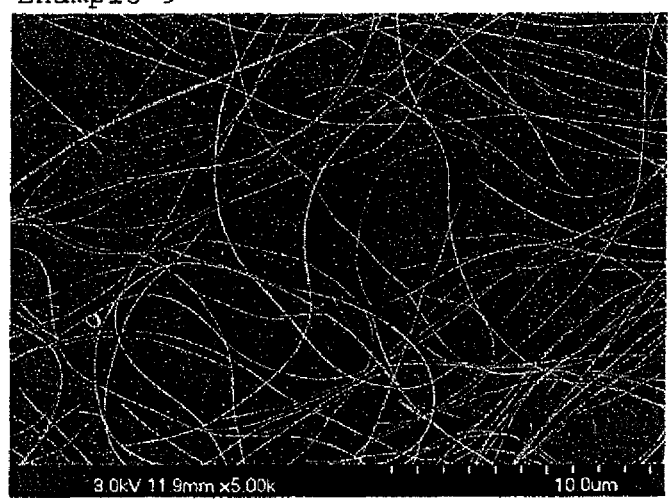

[Fig. 10] Example 10
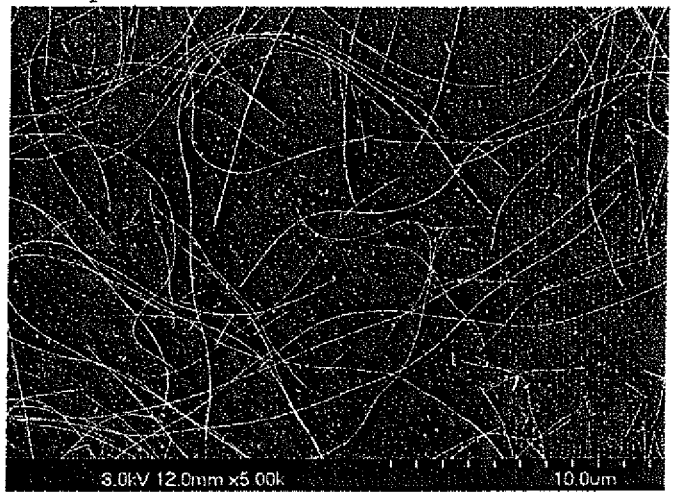
[Fig. 11] Example 11
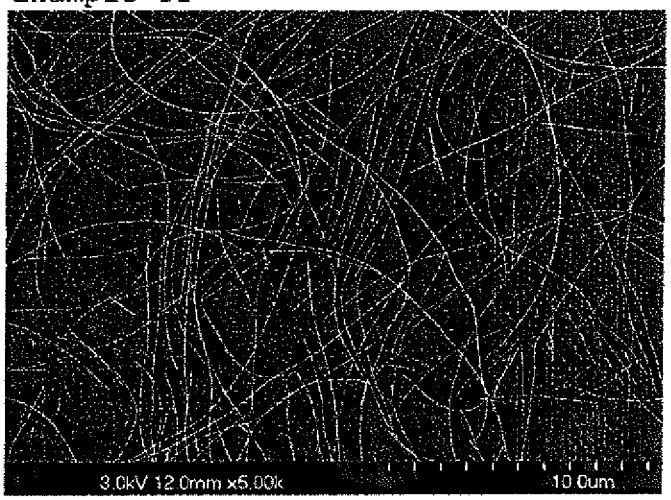
[Fig. 12] Example 12

[Fig.13] Example 13
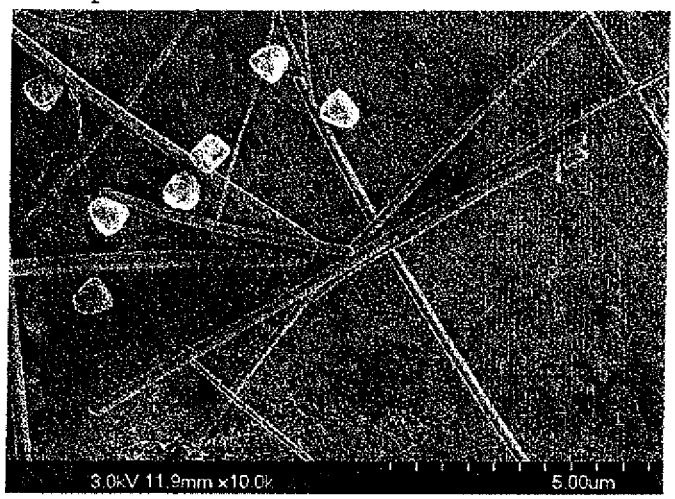
[Fig.14]
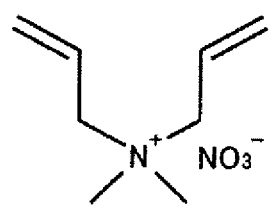
[Fig.15]
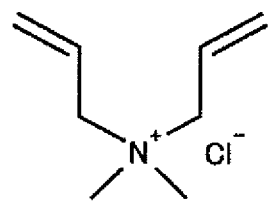

METHOD FOR PRODUCING SILVER NANOWIRES, SILVER NANOWIRES, AND INK USING SAME

This application is a Divisional of U.S. Ser. No. 15/122,200 filed on Aug. 29, 2016, which is a national phase of PCT/JP2015/056162 filed on Mar. 3, 2015.

TECHNICAL FIELD

The present invention relates to a method for producing silver nanowires that are useful as a material for forming a transparent conductor, and the like. The invention also relates to the silver nanowires and a silver nanowires ink using the same.

BACKGROUND ART

In the description herein, an aggregate of minute metal wire having a thickness of approximately 200 nm or less is referred to as "nanowires". When the nanowires are compared to powder, the respective wire correspond to "particle" constituting the powder, and the nanowires correspond to "powder" as an aggregate of particle.

Silver nanowires are expected as a conductive material for imparting conductivity to a transparent substrate. By coating a liquid containing silver nanowires (i.e., a silver nanowires ink) on a transparent substrate, such as glass, PET (polyethylene terephthalate) and PC (polycarbonate), followed by removing the liquid component by evaporation or the like, the silver nanowires are in contact with each other on the substrate to form a conductive network, thereby achieving a transparent conductor. For a transparent conductive material, a metal oxide film represented by ITO has been mainly used for such purposes as a transparent electrode. However, the metal oxide film has defects including the high film forming cost, the low resistance to bending, which may prevent the final product becoming flexible, and the like. A conductive film for a touch-sensitive panel sensor, which is one of the major applications of the transparent conductor, is demanded to have high transparency and high conductivity, and the demand in visibility thereof is also increasing in recent years. An ordinary ITO film necessarily has an increasing thickness for enhancing the conductivity thereof, but the increase of the thickness may decrease the transparency, and the visibility may not be improved.

Silver nanowires are expected to avoid the aforementioned defects peculiar to the metal oxide film represented by ITO.

Known production methods of silver nanowires include a method of dissolving a silver compound in a polyol solvent, such as ethylene glycol and the like, and depositing metallic silver having a linear shape by utilizing the reduction power of the polyol as the solvent in the presence of a halogen compound and PVP (polyvinylpyrrolidone) as a protective agent (PTLs 1 and 2 and NPL 1).

CITATION LIST

Patent Literatures

PTL 1: US 2005/0056118
PTL 2: US 2008/0003130

Non-Patent Literature

NPL 1: J. of Solid State Chem., 1992, 100, 272-280

SUMMARY OF INVENTION

Technical Problem

Silver nanowires having a surface protected with PVP are obtained by the aforementioned known method. PVP is a useful substance for synthesizing silver nanowires with good yield, and many case examples have been presented in literatures and the like.

For achieving both high transparency and high conductivity, silver nanowires advantageously have a smaller diameter and a larger length. The ordinary silver nanowires synthesized by using PVP are not necessarily satisfactory in consideration of the demanded characteristics which are expected to be more severe in such purposes as a touch-sensitive panel sensor (i.e., the achievement of both transparency and conductivity at higher levels).

Furthermore, the silver nanowires synthesized by using PVP are also demanded to be improved in dispersion stability of the silver nanowires in a liquid solvent. Specifically, there is a problem that the silver nanowires in the form of an ink are liable to be precipitated. The dispersibility of silver nanowires in the liquid solvent largely depends on the species of the protective agent. More specifically, the dispersibility depends on the extent of the difference in solubility parameter between the solvent and the silver nanowires, and the electrostatic repulsive force, the steric hindrance effect and the like of the organic protective agent.

The invention describes a novel technique for stably producing thin and long silver nanowires. The invention is to provide, by the technique, silver nanowires that are effective for improving the dispersion stability in a liquid solvent.

Solution to Problem

For achieving the objects, the invention provides a method for producing silver nanowires, containing reduction-depositing silver in the form of wire in an alcohol solvent having dissolved therein a silver compound, the deposition being performed in the alcohol solvent having dissolved therein a chloride, a bromide, an alkali metal hydroxide, an aluminum salt, and an organic protective agent, the molar ratio Al/OH of the total Al amount of the aluminum salt dissolved in the solvent and the total hydroxide ion amount of the alkali metal hydroxide dissolved therein being from 0.01 to 0.40, the molar ratio OH/Ag of the total hydroxide ion amount of the alkali metal hydroxide dissolved in the solvent and the total Ag amount of the silver compound dissolved therein being from 0.005 to 0.50.

The organic protective agent used may be a copolymer of vinylpyrrolidone and an another monomer. The polymerization composition thereof may be, for example, preferably from 0.1 to 10% by mass of the another monomer and the balance of vinylpyrrolidone. The another monomer is preferably a cationic monomer. Specific examples of the another monomer include a diallyldimethylammonium salt monomer.

The alcohol as a solvent is preferably a glycol compound. Examples thereof include ethylene glycol, propylene glycol (1,2-propanediol), 1,3-propanediol, 1,3-butanediol, 1,4-butanediol, and glycerin. An alcohol solvent containing one kind or two or more kinds of an alcohol may be used.

The alkali metal hydroxide used may be, for example, one or more of lithium hydroxide, sodium hydroxide, and potassium hydroxide.

Examples of the aluminum salt include aluminum nitrate and aluminum chloride. In the case where aluminum chloride is used, a part or the whole of the chloride described later may be covered thereby.

The chloride used may be, for example, one or more of chlorides of hydrogen, lithium, sodium, potassium, and copper.

The bromide used may be, for example, one or more of bromides of hydrogen, lithium, sodium, and potassium.

The silver compound used may be silver nitrate.

The reduction deposition of silver is preferably performed in a temperature range of 60° C. or more and the boiling point of the alcohol solvent used or less.

According to the production method, silver nanowires having an average diameter of 50 nm or less and an average length of 10 μm or more can be obtained. Assuming that the ratio of the average length (nm) and the average diameter (nm) is referred to as an average aspect ratio, the average aspect ratio is particularly preferably 250 or more. The average diameter, the average length, and the average aspect ratio accord to the following definitions.

Average Diameter

In a projected image of one metal wire on a micrograph (for example, an FE-SEM micrograph), the diameters of inscribed circles tangent to the contours on both sides in the thickness direction are measured over the entire length of the wire, and the average value of the diameters is designated as the average diameter of the wire. The average value of the diameters of the respective wires constituting the nanowires is designated as the average diameter of the nanowires. The total number of the wires to be measured for calculating the average diameter is 100 or more.

Average Length

In a projected image of one metal wire on a micrograph as similar to the above, the length of the line passing through the center of the thickness of the wire (i.e., the center of the inscribed circle) from one end to the other end of the wire is designated as the length of the wire. The average value of the lengths of the respective wires constituting the nanowires is designated as the average length of the nanowires. The total number of the wires to be measured for calculating the average length is 100 or more.

The silver nanowires according to the invention are constituted by wires each having an extremely long and thin shape. Therefore, the silver nanowires thus recovered often exhibit a curved string form rather than a straight rod form. The inventors have developed a software for measuring the wire length efficiently on the image for the curved wires, and have utilized the software for processing the data.

Average Aspect Ratio

The average diameter and the average length are substituted into the following expression (1) to calculate the average aspect ratio.

$$\text{(average aspect ratio)} = \text{(average length (nm))} / \text{(average diameter (nm))} \quad (1)$$

When silver nanowires are synthesized by the production method, the surface of the wires is covered with the organic protective agent used. According to the invention, silver nanowires that are covered with a cationic organic protective agent can also be obtained. In particular, silver nanowires that are covered with a copolymer of vinylpyrrolidone and an another monomer, preferably a copolymer of vinylpyrrolidone and an additional cationic monomer, can be provided. Examples thereof include silver nanowires that are covered with a copolymer of vinylpyrrolidone and a diallyldimethylammonium salt monomer. According to the production method, metal nanowires that contain Al in a mass proportion of from 100 to 1,000 ppm based on the metal elements can be obtained.

According to the invention, furthermore, a silver nanowires ink is provided that contains the silver nanowires obtained by the production method in an amount of 0.05 to 5.0% by mass in a liquid solvent.

Advantageous Effects of Invention

According to the invention, silver nanowires that are thin and long can be stably produced. In particular, silver nanowires having an average diameter of 50 nm or less, an average length of 10 μm or more, and an average aspect ratio of 250 or more can be produced relatively easily. The thin and long silver nanowires are advantageous for enhancing transparency and conductivity of a transparent conductor. Furthermore, the use of an aluminum salt enables synthesis of silver nanowires with good yield having an organic protective agent other than PVP applied thereto. Accordingly, a silver nanoink improved in dispersion stability can be obtained. The silver nanoink having improved dispersion stability enhances the time margin for avoiding precipitation and localization of the wires in the process of coating the ink on a transparent substrate, and thus is significantly useful for producing a transparent conductor with high quality at low cost.

BRIEF DESCRIPTION OF DRAWINGS

FIG. 1 is an SEM micrograph of the silver nanowires obtained in Example 1.

FIG. 2 is an SEM micrograph of the silver nanowires obtained in Example 2.

FIG. 3 is an SEM micrograph of the silver nanowires obtained in Example 3.

FIG. 4 is an SEM micrograph of the silver nanowires obtained in Example 4.

FIG. 5 is an SEM micrograph of the silver nanowires obtained in Example 5.

FIG. 6 is an SEM micrograph of the silver nanowires obtained in Example 6.

FIG. 7 is an SEM micrograph of the silver nanowires obtained in Example 7.

FIG. 8 is an SEM micrograph of the silver nanowires obtained in Example 8.

FIG. 9 is an SEM micrograph of the silver nanowires obtained in Example 9.

FIG. 10 is an SEM micrograph of the silver nanowires obtained in Example 10.

FIG. 11 is an SEM micrograph of the silver nanowires obtained in Example 11.

FIG. 12 is an SEM micrograph of the silver nanowires obtained in Comparative Example 2.

FIG. 13 is an SEM micrograph of the silver particles obtained in Comparative Example 6.

FIG. 14 is the structural formula of diallyldimethylammonium nitrate.

FIG. 15 is the structural formula of diallyldimethylammonium chloride.

DESCRIPTION OF EMBODIMENTS

Alcohol Solvent

In the invention, such a measure is applied that in an alcohol solvent, silver is deposited by utilizing the reduction power of alcohol. The kind of the alcohol may be selected in such a manner that the alcohol has suitable reduction power to silver, and is capable of depositing metallic silver in a wire form. Under the current situation, it has been said that a polyol, represented by ethylene glycol, is relatively suitable for the formation of silver nanowires, but it is considered that larger kinds of alcohol compounds may be confirmed as applicable by the future researches. The inventors have succeeded at the synthesis of thin and long silver nanowires in an alcohol solvent containing one or more of ethylene glycol, propylene glycol (1,2-propanediol), 1,3-propanediol, 1,3-butanediol, 1,4-butanediol, and glycerin, in an industrially practicable yield. These alcohols may be used solely or as a mixture of two or more kinds thereof.

Silver Compound

A silver compound that is soluble in the solvent is used as a silver source for the reduction deposition of silver nanowires. Examples thereof include silver nitrate, silver acetate, silver oxide, and silver chloride, and silver nitrate ($AgNO_3$) is conveniently used in consideration of the solubility in the solvent and the cost. The amount of Ag added to the total amount of the alcohol solvent used is preferably in a range of from 0.001 to 0.1 mol of Ag, and more preferably in a range of from 0.025 to 0.080 mol of Ag, per 1 L of the solvent.

Chloride

For reduction deposition of metallic silver in a wire form in the alcohol solvent, the presence of a chloride ion having a function of imparting anisotropy to the growing direction in the deposition is necessary. It is considered that the chloride ion quickly etches a particular crystal face of metallic silver formed through nucleation to facilitate formation of multiple twinning, thereby enhancing the proportion of the crystal nuclei forming the wires. As the chloride ion source, various materials may be used that are chlorides soluble in the alcohol as the solvent. TBAC (tetrabutylammonium chloride, $(CH_3CH_2CH_2CH_2)_4NCl$), which is an organic chlorine compound, may also be used. Preferred examples thereof include sodium chloride (NaCl), potassium chloride (KCl), hydrogen chloride (HCl), and lithium chloride (LiCl), which are industrially easily available and are inexpensive. Copper(II) chloride ($CuCl_2$), which is soluble in the alcohol solvent, may be used. The amount of the chloride added based on the total amount of the alcohol solvent used is preferably in a range of from 0.00001 ($1\times10^{-5}$) to 0.01 mol, and more preferably in a range of from 0.00005 ($5\times10^{-5}$) to 0.01 mol, in terms of Cl amount per 1 L of the solvent.

Bromide

A bromide ion also has a function of imparting anisotropy to the growing direction in the deposition of metallic silver. As a result of various investigations, it has been found that the bromide ion that is present in the alcohol solvent in addition to the chloride ion is significantly effective for providing thin and long silver nanowires having, for example, an average diameter of 50 nm or less and an average length of 10 μm or more. As a bromide ion source, various materials may be used that are bromides soluble in the alcohol as the solvent. CTAB (cetyltrimethylammonium bromide, $(C_{16}H_{33})N(CH_3)_3Br$), which is an organic bromine compound, may also be used. Preferred examples thereof include sodium bromide (NaBr), potassium bromide (KBr), hydrogen bromide (HBr), and lithium bromide (LiBr), which are industrially easily available and are inexpensive. The amount of the bromide added may be extremely small, but the bromide is an extremely effective additive for imparting anisotropy. The amount of the bromide added based on the total amount of the alcohol solvent used is preferably in a range of from 0.000001 ($1\times10^{-6}$) to 0.001 ($1\times10^{-3}$) mol, and more preferably in a range of from 0.000005 ($5\times10^{-6}$) to 0.001 ($1\times10^{-3}$) mol, in terms of Br amount per 1 L of the solvent.

Aluminum Salt and Alkali Metal Hydroxide

The inventors have found that silver nanowires having a large aspect ratio can be effectively synthesized by dissolving an aluminum salt and an alkali metal hydroxide in prescribed ratios in the solvent, in which silver is deposited. While the mechanism of the phenomenon is not clear under the current circumstances, it is expected that an aluminum ion is expected to have a function of activating the crystal face for growing silver in a wire form, and a function of enhancing the reducing rate, and it is considered that the functions are exhibited in the appropriate presence of a hydroxide ion.

The presence of Al is confirmed in the silver nanowires synthesized in the solvent containing the aluminum salt. As a result of the researches by the inventors, there is a tendency that metal nanowires containing Al in an amount of from 100 to 1,000 ppm in the metal components have high uniformity in diameter and are hard to suffer local breakage or bending irrespective of the thin and long form thereof. These silver nanowires are excellent in handleability in the operation of forming an ink and the operation of coating on a substrate. The silver nanowires preferably contain Al in an amount of 150 ppm or more, and more preferably from 200 to 800 ppm.

In the description herein, the molar ratio of the total Al amount of the aluminum salt dissolved in the solvent and the total hydroxide ion amount of the alkali metal hydroxide dissolved therein is expressed by "Al/OH", and the molar ratio may be hereinafter referred simply to as "Al/OH molar ratio". As a result of detailed investigations, thin and long silver nanowires can be synthesized by an Al/OH molar ratio of from 0.01 to 0.40. When the Al/OH molar ratio is too large, the reduction power of the alcohol solvent may be decreased, and the silver ion or the silver complex dissolved in the solvent may not be reduced to the metallic silver. When the Al/OH molar ratio is too small, it may be difficult to synthesize long wires having a large average aspect ratio.

Even in the case where the Al/OH molar ratio is in the appropriate range, however, when the amount of the alkali hydroxide is too large with respect to silver, a large amount of the synthesis product mainly containing silver oxide is formed, thereby failing to synthesis wires. When the amount of alkali hydroxide is too small with respect to silver, on the other hand, it may be difficult to cause the reduction reaction of silver. In the description herein, the molar ratio of the total hydroxide ion amount of the alkali metal hydroxide dissolved in the solvent and the total Ag amount of the silver compound dissolved therein is expressed by "OH/Ag", and the molar ratio may be hereinafter referred simply to as "OH/Ag molar ratio". As a result of detailed investigations, the OH/Ag molar ratio is desirably in a range of from 0.005 to 0.50.

The alkali metal hydroxide used is industrially preferably one or more of lithium hydroxide, sodium hydroxide, and potassium hydroxide.

The aluminum salt used may be aluminum nitrate and aluminum chloride. Aluminum nitrate may be added in the form of aluminum nitrate nonahydrate $Al(NO_3)_3 \cdot 9H_2O$. In the case where aluminum chloride is used, aluminum chloride may cover the aforementioned chloride.

Organic Protective Agent

The organic protective agent has a function of covering the surface of silver nanowires deposited through the reduction reaction and preventing the silver nanowires from growing coarsely. The organic protective agent present on the surface of the resulting silver nanowires has a function of ensuring the dispersibility thereof in a liquid medium. PVP (polyvinylpyrrolidone) has been known as an organic protective agent that is effective for synthesizing silver nanowires through deposition of silver preferentially in only one direction. However, silver nanowires that are synthesized by using PVP are difficult to form a silver nanowires ink having good dispersion stability. Specifically, the silver nanowires in the form of ink are liable to be precipitated.

The inventors have found that when reduction deposition of silver is performed in the state where the aluminum salt is dissolved, the tendency of deposition of silver only in one direction is enhanced, and thereby thin and long silver nanowires having a favorable shape can be synthesized with good yield even in the case where PVP is not used as an organic protective agent. As a novel organic protective agent that is applicable instead of PVP, there may be a possibility that various materials may be confirmed as a result of the future development of researches. Under the current situation, a copolymer having a polymerization composition containing vinylpyrrolidone and an another monomer is significantly effective. The polymerization composition thereof is preferably from 0.1 to 10% by mass of an additional cationic monomer and the balance of vinylpyrrolidone. The polymerization composition means that the copolymer has a structure containing the monomers copolymerized with each other, and it is not limited as to whether or not the actual production process thereof is performed through a polymerization reaction process of the monomers.

In the invention, the organic protective agent that contains a cationic monomer as the another monomer may be particularly used. In this case, the copolymer exhibits cationic property. The silver nanowires that are covered with the organic protective agent of this type have a larger electrostatic repulsive force than PVP in a liquid medium having large polarity, such as water and an alcohol, and thus exhibit excellent dispersion stability therein. When a solvent substance having small polarity is added to the liquid medium showing the excellent dispersibility, the silver nanowires are quickly aggregated. By utilizing the property, the silver nanowires are quickly aggregated, for example, by adding a liquid having small polarity, such as acetone, toluene, hexane, and kerosene, to the alcohol solvent after synthesizing the silver nanowires, to reduce the polarity of the solvent and therefore industrially excellent characteristics, such as significant simplicity in washing and recovering, can be provided. It has been also confirmed that a solvent having large polarity, such as water, is again added to the aggregated material, the good dispersibility is exhibited. Examples of the cationic organic protective agent include one having a polymerization composition containing vinylpyrrolidone and a diallyldimethylammonium salt monomer.

Production Method

A method of providing silver nanowires in an alcohol solvent having a silver compound dissolved therein, through the reduction power of the alcohol as the solvent in the presence of a halogen compound and an organic protective agent has been known. In this case, it is said that PVP is suitable as the organic protective agent for depositing metallic silver in a wire form. In the invention, silver nanowires are formed by utilizing the reduction power of the alcohol solvent. However, silver is reduction-deposited under the state where a chloride, a bromide, an aluminum salt, an alkali metal hydroxide, and an organic protective agent are dissolved in the alcohol solvent. At this time, as described above, the molar ratio Al/OH of the total Al amount of the aluminum salt dissolved in the solvent and the total hydroxide ion amount of the alkali metal hydroxide dissolved therein is from 0.01 to 0.40, and the molar ratio OH/Ag of the total hydroxide ion amount of the alkali metal hydroxide dissolved in the solvent and the total Ag amount of the silver compound dissolved therein is from 0.005 to 0.50.

The temperature where the reduction deposition reaction of silver is performed may be set in a range of 60° C. or more and a boiling point of the solvent used or less. The boiling point herein is a boiling point under the pressure of the gas phase space in contact with the liquid surface of the solvent inside the reaction vessel. In the case where plural kinds of alcohols are used as the solvent, the temperature may be the boiling point of the alcohol having the lowest boiling point or less. From the standpoint that the reaction is performed moderately, however, the temperature is preferably controlled to a temperature lower than the boiling point for avoiding boiling. In the case where ethylene glycol is used as the solvent, and the reaction is performed under the atmospheric pressure, for example, the reaction is preferably performed at a temperature of from 60 to 185° C., and more preferably from 80 to 175° C., while ethylene glycol has a boiling point of approximately 197° C. The reaction time may be in a range of from 10 to 1,440 minutes.

As for the procedures, it is preferred that the substances except for the silver compound are dissolved in the alcohol solvent, and after the temperature of the solvent (which is hereinafter referred to as a solution A) reaches the prescribed reaction temperature, the silver compound is added to the solution A. The silver compound may be added in such a manner that the silver compound is dissolved in an alcohol solvent of the same kind as the aforementioned solvent in advance, and the silver-containing liquid (which is hereinafter referred to as a solution B) is mixed in the solution A. The solution B before mixing in the solution A preferably has a temperature around ordinary temperature (for example, from 15 to 40° C.). When the temperature of the solution B is too low, a long period of time may be required for dissolving the silver compound, and when the temperature thereof is too high, the reduction reaction of silver tends to occur before the step of mixing in the solution A due to the reduction power of the alcohol solvent in the solution B. A silver compound that is easily dissolved in the alcohol solvent, such as silver nitrate, may be added in the form of solid to the solution A. The method of adding the silver compound may be a method of adding the entire amount thereof at one time, and a method of adding intermittently or continuously over a certain period of time. The liquid is continuously stirred while the reaction proceeds. The atmosphere of the gas phase in contact with the liquid surface of the solution A while the reaction proceeds may be the air atmosphere or nitrogen.

After completing the deposition reaction of silver, a slurry containing silver nanowires is subjected to solid-liquid separation by such a measure as centrifugal separation or decantation, so as to recover the solid matter. The decantation may be performed by condensing while still standing over approximately 2 weeks, or by condensing through the enhancement of the sedimentation rate by adding at least one of a solvent having small polarity, such as acetone, toluene, hexane, and kerosene, thereto. In the case of centrifugal separation, the slurry after the reaction may be subjected directly to a centrifugal separator, so as to condense the silver nanowires.

After condensing, the supernatant is removed. Thereafter, a solvent having large polarity, such as water and an alcohol, is added for redispersing the silver nanowires, and the solid matter is recovered by solid-liquid separation by such a measure as centrifugal separation or decantation. The procedure of redispersion and condensing (i.e., washing) is preferably performed repeatedly.

The solid matter after washing contains mainly the silver nanowires having the organic protective agent on the surface thereof. The silver nanowires may be stored in the form of a dispersion liquid containing the silver nanowires dispersed in a suitable liquid medium depending on the purpose. The silver nanowire dispersion liquid may be utilized as a supply source of silver nanowires in various purposes.

To the silver nanowire dispersion liquid, a viscosity modifier may be added for controlling the viscosity suitably corresponding to the system of the coating device and the printing device, and a binder may be added depending on necessity for ensuring the adhesiveness to the substrate. A dispersant and the like may be further added depending on necessity. Thus, a silver nanoink suitable for various purposes may be provided in this manner. The content of the silver nanowires in the silver nanowires ink may be controlled, for example, in a range of from 0.05 to 5.0% by mass.

The silver nanowires ink may be coated on the transparent substrate, such as a PET film, PC, and glass, and then the liquid component may be removed by drying through evaporation, thereby producing a transparent conductor.

Dispersion Stability of Silver Nanoink

The dispersion stability can be evaluated in such a manner that while a container having the thus-produced silver nanowires ink housed therein is allowed to stand still, the silver nanowires ink immediately after production and that after the prescribed period of time each are coated on a substrate to form dried coated films, and the dried coated films are measured for sheet resistance. With an ink having good dispersion stability of the silver nanowires, the sheet resistance values obtained by coating the inks immediately after the production, after 4 hours, and after 8 hours are the same as each other without substantially any difference. With an ink having poor dispersion stability, the concentration of the silver nanowires dispersed in the ink is lowered due to precipitation of the silver nanowires, and the sheet resistance value is increased in the inks with an increased elapsed time, i.e., 4 hours and 8 hours. The ink having poor dispersion stability in a container is confirmed by visual observation to form a transparent supernatant after 8 hours.

The dispersion stability is significantly important in the production of a transparent conductor. One of the important purposes of silver nanowires is a transparent conductive film. In the production process thereof, a silver nanoink is continuously coated on a PET film as a transparent substrate with a coating device in a roll-to-roll process, and the continuous coating time may be half a day at the longest. While the silver nanowires ink is housed in the ink tank of the coating device during that period of time, the silver nanowires may be precipitated and aggregated in the ink tank if the silver nanowires have poor dispersion stability, and thus it may be difficult to form a coated layer having stable quality.

EXAMPLES

Example 1

Ethylene glycol as the alcohol solvent, silver nitrate as the silver compound, sodium chloride as the chloride, sodium bromide as the bromide, sodium hydroxide as the alkali metal hydroxide, aluminum nitrate nonahydrate as the aluminum salt, and a copolymer of vinylpyrrolidone and diallyldimethylammonium nitrate (the structural formula of which is shown in FIG. 14) (the copolymer was formed with 99% by mass of vinylpyrrolidone and 1% by mass of diallyldimethylammonium nitrate, weight average molecular weight: 130,000) as the organic protective agent were prepared.

At room temperature, to 540 g of ethylene glycol, 0.041 g of sodium chloride, 0.0072 g of sodium bromide, 0.0506 g of sodium hydroxide, 0.0416 g of aluminum nitrate nonahydrate, and 5.24 g of the copolymer of vinylpyrrolidone and diallyldimethylammonium nitrate were added and dissolved to prepare a solution A. In a vessel separate therefrom, 4.25 g of silver nitrate was added and dissolved in 20 g of ethylene glycol to prepare a solution B.

In this example, the Al/OH molar ratio (described above) is 0.0876, and the OH/Ag molar ratio (described above) is 0.0506.

The entire amount of the solution A was heated from ordinary temperature to 115° C. under stirring, and then the entire amount of the solution B was added to the solution A over 1 minute. After completing the addition of the solution B, the solution was retained at 115° C. for 24 hours while retaining the stirring condition. Thereafter, the reaction liquid was cooled to room temperature. After cooling, acetone in an amount 10 times the amount of the reaction liquid was added to the reaction liquid, and the reaction liquid was stirred for 10 minutes and then allowed to stand still for 24 hours. After standing still, a condensed matter and a supernatant were observed, and the supernatant was carefully removed with a pipette to provide a condensed matter.

500 g of pure water was added to the resulting condensed matter, which was dispersed by stirring for 10 minutes, and then acetone in an amount of 10 times was added thereto, followed by stirring and then allowing to stand still for 24 hours. After standing still, a condensed matter and a supernatant were again observed, and the supernatant was carefully removed with a pipette. The excessive organic protective agent is unnecessary for providing good conductivity. Thus, the washing operation was performed 1 to approximately 20 times depending on necessity, thereby sufficiently washing the solid matter.

Pure water was added to the solid matter after washing to provide a dispersion liquid of the solid matter. The dispersion liquid was collected, and the observation of the dispersion liquid after evaporating pure water as a solvent on an observation stand with a high resolution FE-SEM (high resolution field emission scanning electron microscope) revealed that the solid matter was silver nanowires. FIG. 1 exemplifies the SEM micrograph of the silver nanowires. In the SEM observation, all the silver nanowires observed in five view fields selected arbitrarily were measured, and the average diameter and the average length were obtained according to the definitions described above. The total number of wires measured was 100 or more. The diameter was measured with micrographs imaged with the high resolution SEM at a magnification of 150,000, and the length was measured with micrographs imaged with the high resolution SEM at a magnification of 2,500.

As a result, the average diameter was 45 nm, the average length was 15 μm, and the average aspect ratio was 15,000 nm/45 nm≈333.

A solvent having a mass ratio of pure water/isopropyl alcohol of 8/2 was added to the solid matter after washing, and hydroxypropyl methyl cellulose as a thickener was added to make a viscosity of 35 mPas with a rotation viscometer (HAAKE RheoStress 600, produced by Thermo Scientific, Inc., measurement cone: cone C60/1°, Ti, (D=60 mm), plate: Meas. Plate cover MPC60) at 50 rpm, thereby producing an ink. The ink was regulated to have a silver nanowire content of 0.3% by mass. The silver nanowires ink was coated on a surface of a PET film (Lumirror UD03, produced by Toray Industries, Inc.) having a size of 5 cm×5 cm with a bar coater No. 7, and dried at 120° C. for 1 minute. The sheet resistance of the dried coated film was measured with Loresta HP MCP-T410, produced by Mitsubishi Chemical Analytech Co., Ltd. The total light transmittance of the dried coated film was measured with Haze Meter NDH 5000, produced by Nippon Denshoku Industries Co., Ltd.

As a result, the sheet resistance immediately after the production of the ink was 46Ω per square, and the total light transmittance immediately after the production thereof was 90.9% (the total light transmittance including the PET substrate). These values show excellent characteristics that sufficiently satisfy the demanded characteristics of a transparent conductive film for a touch-sensitive panel sensor.

Thereafter, while the ink was allowed to stand still in a container, the ink was collected after 4 hours and 8 hours from the specimen collecting port provided at a height of 1 cm from the bottom of the container, and coated and dried on the PET film in the same manner as above, and the sheet resistance and the total light transmittance were measured.

As a result, the sheet resistance after 4 hours was 47Ω per square, and the total light transmittance after 4 hours was 90.9%. The sheet resistance after 4 hours was 43Ω per square, and the total light transmittance after 4 hours was 90.7%. It was thus confirmed that the silver nanowires were present stably in the ink, and the silver nanoink had high dispersion stability.

The silver nanowires of this example were thermally decomposed with 60% nitric acid to form a solution, which was then measured for the Al content by the ICP atomic emission spectroscopic analysis method (device: ICP atomic emission spectroscopic analyzer 720-ES, produced by Agilent Technologies Inc.), and as a result, the Al content in the metal components was 430 ppm.

Example 2

The experiment was performed under the same conditions as in Example 1 except that in the synthesis of the silver nanowires, 0.0527 g of potassium chloride as the chloride, 0.0083 g of potassium bromide as the bromide, and 0.0710 g of potassium hydroxide as the alkali metal hydroxide were added.

In this example, the Al/OH molar ratio is 0.0876, and the OH/Ag molar ratio is 0.0506.

As a result of SEM observation, the formation of silver nanowires was observed, in which the average diameter was 41 nm, the average length was 12 μm, and the average aspect ratio was 12,000 nm/41 nm≈293.

FIG. 2 exemplifies the SEM micrograph of the silver nanowires.

The silver nanowires of this example were measured for the Al content in the same manner as in Example 1, and as a result, the Al content in the metal components was 440 ppm.

Example 3

The experiment was performed under the same conditions as in Example 1 except that in the synthesis of the silver nanowires, 0.030 g of lithium chloride as the chloride, 0.0083 g of potassium bromide as the bromide, and 0.030 g of lithium hydroxide as the alkali metal hydroxide were added.

In this example, the Al/OH molar ratio is 0.0876, and the OH/Ag molar ratio is 0.0506.

As a result of SEM observation, the formation of silver nanowires was observed, in which the average diameter was 41 nm, the average length was 12 μm, and the average aspect ratio was 12,000 nm/41 nm≈293.

FIG. 3 exemplifies the SEM micrograph of the silver nanowires.

The silver nanowires of this example were measured for the Al content in the same manner as in Example 1, and as a result, the Al content in the metal components was 530 ppm.

Example 4

Propylene glycol (1,2-propanediol) as the alcohol solvent, silver nitrate as the silver compound, lithium chloride as the chloride, potassium bromide as the bromide, lithium hydroxide as the alkali metal hydroxide, aluminum nitrate nonahydrate as aluminum nitrate, and a copolymer of vinylpyrrolidone and diallyldimethylammonium nitrate (the copolymer was formed with 99% by mass of vinylpyrrolidone and 1% by mass of diallyldimethylammonium nitrate, weight average molecular weight: 130,000) as the organic protective agent were prepared.

At room temperature, to 500 g of propylene glycol, 0.030 g of lithium chloride, 0.00832 g of potassium bromide, 0.0075 g of lithium hydroxide, 0.0416 g of aluminum nitrate nonahydrate, and 5.24 g of the copolymer of vinylpyrrolidone and diallyldimethylammonium nitrate were added and dissolved to prepare a solution A. In a vessel separate therefrom, 4.25 g of silver nitrate was added and dissolved in 20 g of propylene glycol to prepare a solution B.

In this example, the Al/OH molar ratio is 0.0876, and the OH/Ag molar ratio is 0.0127.

The experiment was performed under the same conditions as in Example 1 except for the above.

As a result of SEM observation, the formation of silver nanowires was observed, in which the average diameter was 48 nm, the average length was 30 μm, and the average aspect ratio was 30,000 nm/48 nm=625.

FIG. 4 exemplifies the SEM micrograph of the silver nanowires.

The silver nanowires of this example were measured for the Al content in the same manner as in Example 1, and as a result, the Al content in the metal components was 200 ppm.

Example 5

The experiment was performed under the same conditions as in Example 4 except that in the synthesis of the silver nanowires, 0.120 g of lithium hydroxide as the alkali metal hydroxide, and 0.4992 g of aluminum nitrate nonahydrate as the aluminum salt were added.

In this example, the Al/OH molar ratio is 0.2628, and the OH/Ag molar ratio is 0.2025.

As a result of SEM observation, the formation of silver nanowires was observed, in which the average diameter was 38 nm, the average length was 17 μm, and the average aspect ratio was 17,000 nm/38 nm≈447.

FIG. 5 exemplifies the SEM micrograph of the silver nanowires.

The silver nanowires of this example were measured for the Al content in the same manner as in Example 1, and as a result, the Al content in the metal components was 750 ppm.

Example 6

The experiment was performed under the same conditions as in Example 4 except that in the synthesis of the silver nanowires, 0.030 g of lithium hydroxide as the alkali metal hydroxide, and 0.1248 g of aluminum nitrate nonahydrate as the aluminum salt were added.

In this example, the Al/OH molar ratio is 0.2628, and the OH/Ag molar ratio is 0.0506.

As a result of SEM observation, the formation of silver nanowires was observed, in which the average diameter was 43 nm, the average length was 29 μm, and the average aspect ratio was 29,000 nm/43 nm≈674.

FIG. 6 exemplifies the SEM micrograph of the silver nanowires.

The silver nanowires of this example were measured for the Al content in the same manner as in Example 1, and as a result, the Al content in the metal components was 570 ppm.

Example 7

The experiment was performed under the same conditions as in Example 4 except that in the synthesis of the silver nanowires, 0.030 g of lithium hydroxide as the alkali metal hydroxide was added.

In this example, the Al/OH molar ratio is 0.0876, and the OH/Ag molar ratio is 0.0506.

As a result of SEM observation, the formation of silver nanowires was observed, in which the average diameter was 31 nm, the average length was 15 μm, and the average aspect ratio was 15,000 nm/31 nm≈484.

FIG. 7 exemplifies the SEM micrograph of the silver nanowires.

The silver nanowires of this example were measured for the Al content in the same manner as in Example 1, and as a result, the Al content in the metal components was 410 ppm.

Example 8

The experiment was performed under the same conditions as in Example 4 except that in the synthesis of the silver nanowires, 0.0225 g of lithium hydroxide as the alkali metal hydroxide, and 0.0052 g of aluminum nitrate nonahydrate as the aluminum salt were added.

In this example, the Al/OH molar ratio is 0.0146, and the OH/Ag molar ratio is 0.0380.

As a result of SEM observation, the formation of silver nanowires was observed, in which the average diameter was 32 nm, the average length was 17 μm, and the average aspect ratio was 17,000 nm/32 nm≈531.

FIG. 8 exemplifies the SEM micrograph of the silver nanowires.

The silver nanowires of this example were measured for the Al content in the same manner as in Example 1, and as a result, the Al content in the metal components was 300 ppm.

Example 9

1,3-Propanediol as the alcohol solvent, silver nitrate as the silver compound, sodium chloride as the chloride, sodium bromide as the bromide, sodium hydroxide as the alkali metal hydroxide, aluminum nitrate nonahydrate as aluminum nitrate, and a copolymer of vinylpyrrolidone and diallyldimethylammonium nitrate (the copolymer was formed with 99% by mass of vinylpyrrolidone and 1% by mass of diallyldimethylammonium nitrate, weight average molecular weight: 130,000) as the organic protective agent were prepared.

At room temperature, to 500 g of 1,3-propanediol, 0.0413 g of sodium chloride, 0.0072 g of sodium bromide, 0.0253 g of sodium hydroxide, 0.0104 g of aluminum nitrate nonahydrate, and 5.24 g of the copolymer of vinylpyrrolidone and diallyldimethylammonium nitrate were added and dissolved to prepare a solution A. In a vessel separate therefrom, 4.25 g of silver nitrate was added and dissolved in 20 g of 1,3-propanediol to prepare a solution B.

In this example, the Al/OH molar ratio is 0.0438, and the OH/Ag molar ratio is 0.0253.

The experiment was performed under the same conditions as in Example 1 except for the above.

As a result of SEM observation, the formation of silver nanowires was observed, in which the average diameter was 48 nm, the average length was 19 μm, and the average aspect ratio was 19,000 nm/48 nm≈396.

FIG. 9 exemplifies the SEM micrograph of the silver nanowires.

The silver nanowires of this example were measured for the Al content in the same manner as in Example 1, and as a result, the Al content in the metal components was 370 ppm.

Example 10

Glycerin as the alcohol solvent, silver nitrate as the silver compound, sodium chloride as the chloride, sodium bromide as the bromide, sodium hydroxide as the alkali metal hydroxide, aluminum nitrate nonahydrate as aluminum nitrate, and a copolymer of vinylpyrrolidone and diallyldimethylammonium nitrate (the copolymer was formed with 99% by mass of vinylpyrrolidone and 1% by mass of diallyldimethylammonium nitrate, weight average molecular weight: 130,000) as the organic protective agent were prepared.

At room temperature, to 610 g of glycerin, 0.0413 g of sodium chloride, 0.0072 g of sodium bromide, 0.0380 g of sodium hydroxide, 0.0104 g of aluminum nitrate nonahydrate, and 5.24 g of the copolymer of vinylpyrrolidone and diallyldimethylammonium nitrate were added and dissolved to prepare a solution A. In a vessel separate therefrom, 4.25 g of silver nitrate was added and dissolved in 20 g of glycerin to prepare a solution B.

In this example, the Al/OH molar ratio is 0.0292, and the OH/Ag molar ratio is 0.0380.

The experiment was performed under the same conditions as in Example 1 except for the above.

As a result of SEM observation, the formation of silver nanowires was observed, in which the average diameter was 47 nm, the average length was 17 μm, and the average aspect ratio was 17,000 nm/47 nm≈362.

FIG. 10 exemplifies the SEM micrograph of the silver nanowires.

The silver nanowires of this example were measured for the Al content in the same manner as in Example 1, and as a result, the Al content in the metal components was 380 ppm.

Example 11

The experiment was performed under the same conditions as in Example 4 except that a copolymer of vinylpyrrolidone and diallyldimethylammonium chloride (the structural formula of which is shown in FIG. 15) (the copolymer was formed with 99% by mass of vinylpyrrolidone and 1% by mass of diallyldimethylammonium chloride, weight average molecular weight: 100,000) as the organic protective agent was prepared, and in the formation of the solution A, 5.24 g of the organic protective agent was added and dissolved.

In this example, the Al/OH molar ratio is 0.0876, and the OH/Ag molar ratio is 0.0127.

As a result of SEM observation, the formation of silver nanowires was observed, in which the average diameter was 40 nm, the average length was 13 μm, and the average aspect ratio was 13,000 nm/40 nm=325.

FIG. 11 exemplifies the SEM micrograph of the silver nanowires.

The silver nanowires of this example were measured for the Al content in the same manner as in Example 1, and as a result, the Al content in the metal components was 290 ppm.

Comparative Example 1

The experiment was performed under the same conditions as in Example 4 except that in the synthesis of the silver nanowires, 0.00188 g of lithium hydroxide as the alkali metal hydroxide, and 0.0052 g of aluminum nitrate nonahydrate as the aluminum salt were added.

In this example, the Al/OH molar ratio is 0.1752, and the OH/Ag molar ratio is 0.0032.

Due to the too small OH/Ag molar ratio, only an extremely small amount of a solid matter was obtained. It is expected that reduction of silver ion is substantially not performed.

Comparative Example 2

The experiment was performed under the same conditions as in Example 4 except that in the synthesis of the silver nanowires, 0.060 g of lithium hydroxide as the alkali metal hydroxide, and 0.0052 g of aluminum nitrate nonahydrate as the aluminum salt were added.

In this example, the Al/OH molar ratio is 0.0055, and the OH/Ag molar ratio is 0.1013.

As a result of SEM observation, the formation of silver nanowires was observed, in which the average diameter was 25 nm, the average length was 5 μm, and the average aspect ratio was 5,000 nm/25 nm=200. Due to the too small Al/OH molar ratio, the average length was small.

FIG. 12 exemplifies the SEM micrograph of the silver nanowires.

Comparative Example 3

The experiment was performed under the same conditions as in Example 4 except that in the synthesis of the silver nanowires, 0.03 g of lithium hydroxide as the alkali metal hydroxide, and 0.2496 g of aluminum nitrate nonahydrate as the aluminum salt were added.

In this example, the Al/OH molar ratio is 0.5257, and the OH/Ag molar ratio is 0.0506.

Due to the too large Al/OH molar ratio, only an extremely small amount of a solid matter was obtained. It is expected that reduction of silver ion is substantially not performed.

Comparative Example 4

The experiment was performed under the same conditions as in Example 4 except that in the synthesis of the silver nanowires, 0.40 g of lithium hydroxide as the alkali metal hydroxide, and 0.4992 g of aluminum nitrate nonahydrate as the aluminum salt were added.

In this example, the Al/OH molar ratio is 0.0789, and the OH/Ag molar ratio is 0.6751.

A solid matter was recovered, but due to the too large OH/Ag molar ratio, no formation of silver nanowires was confirmed, and only a slight amount of an irregular solid matter was obtained.

Comparative Example 5

The experiment was performed under the same conditions as in Example 4 except that in the synthesis of the silver nanowires, 0.00188 g of lithium hydroxide as the alkali metal hydroxide, and 0.0104 g of aluminum nitrate nonahydrate as the aluminum salt were added.

In this example, the Al/OH molar ratio is 0.3505, and the OH/Ag molar ratio is 0.0032.

As similar to Comparative Example 1, due to the too small OH/Ag molar ratio, only an extremely small amount of a solid matter was obtained. It is expected that reduction of silver ion is substantially not performed.

Comparative Example 6

The experiment was performed under the same conditions as in Example 4 except that in the synthesis of the silver nanowires, the amount of lithium hydroxide added was changed to 0.00375 g, and the aluminum salt was not added.

In this example, the Al/OH molar ratio is 0 (no addition of Al), and the OH/Ag molar ratio is 0.0063.

As a result of SEM observation, the formation of silver particles in the form of thick rod was observed, in which the average diameter was 160 nm, the average length was 11 μm, and the average aspect ratio was 11,000 nm/160 nm≈69. In the case where no Al was added, thin silver nanowires were not able to be synthesized with the organic protective agent used herein. FIG. 13 exemplifies the SEM micrograph of the silver particles.

The silver nanowires of this example were measured for the Al content in the same manner as in Example 1, and as a result, the Al content in the metal components was 40 ppm.

The raw materials used in the examples and the results are listed in Table 1.

TABLE 1

| | Raw material used | | | | | | | Synthesis condition | | Synthesis result | | |
| --- | --- | --- | --- | --- | --- | --- | --- | --- | --- | --- | --- | --- |
| Example No. | Silver compound | Alcohol | Chloride | Bromide | Alkali metal hydroxide | Aluminum salt | Organic protective agent *1 | Al/OH molar ratio | OH/Ag molar ratio | Average diameter (nm) | Average length (μm) | Average aspect ratio |
| Example 1 | silver nitrate | ethylene glycol | sodium chloride | sodium bromide | sodium hydroxide | aluminum nitrate | copolymer A | 0.0876 | 0.0506 | 45 | 15 | 333 |

TABLE 1-continued

| | Raw material used | | | | | | Synthesis condition | | Synthesis result | | |
|---|---|---|---|---|---|---|---|---|---|---|---|
| Example No. | Silver compound | Alcohol | Chloride | Bromide | Alkali metal hydroxide | Aluminum salt | Organic protective agent *1 | Al/OH molar ratio | OH/Ag molar ratio | Average diameter (nm) | Average length (µm) | Average aspect ratio |
| Example 2 | silver nitrate | ethylene glycol | potassium chloride | potassium bromide | potassium hydroxide | aluminum nitrate | copolymer A | 0.0876 | 0.0506 | 41 | 12 | 293 |
| Example 3 | silver nitrate | ethylene glycol | lithium chloride | potassium bromide | litnium hydroxide | aluminum nitrate | copolymer A | 0.0876 | 0.0506 | 41 | 12 | 293 |
| Example 4 | silver nitrate | propylene glycol | lithium chloride | potassium bromide | lithium hydroxide | aluminum nitrate | copolymer A | 0.0876 | 0.0127 | 48 | 30 | 625 |
| Example 5 | silver nitrate | propylene glycol | lithium chloride | potassiam bromide | lithium hydroxide | aluminum nitrate | copolymer A | 0.2628 | 0.2025 | 38 | 17 | 447 |
| Example 6 | silver nitrate | propylene glycol | lithium chloride | potassium bromide | lithium hydroxide | aluminum nitrate | copolymer A | 0.2628 | 0.0506 | 43 | 29 | 674 |
| Example 7 | silver nitrate | propylene glycol | lithium chloride | potassium bromide | lithium hydroxide | aluminum nitrate | copolymer A | 0.0876 | 0.0506 | 31 | 15 | 484 |
| Example 8 | silver nitrate | propylene glycol | lithium chloride | potassium bromide | lithium hydroxide | aluminum nitrate | copolymer A | 0.0146 | 0.0380 | 32 | 17 | 531 |
| Example 9 | silver nitrate | 1,3-propanediol | sodium chloride | sodium bromide | sodium hydroxide | aluminum nitrate | copolymer A | 0.0438 | 0.0253 | 48 | 19 | 396 |
| Example 10 | silver nitrate | glycerin | sodium chloride | sodium bromide | sodium hydroxide | aluminum nitrate | copolymer A | 0.0292 | 0.0380 | 47 | 17 | 362 |
| Example 11 | silver nitrate | propylene glycol | lithium chloride | potassium bromide | lithium hydroxide | aluminum nitrate | copolymer B | 0.0876 | 0.0127 | 40 | 13 | 325 |
| Comparative Example 1 | silver nitrate | propylene glycol | lithium chloride | potassium bromide | lithium hydroxide | aluminum nitrate | copolymer A | 0.1752 | 0.0032 | (not reduced) | | |
| Comparative Example 2 | silver nitrate | propylene glycol | lithium chloride | potassium bromide | lithium hydroxide | aluminum nitrate | copolymer A | 0.0055 | 0.1013 | 25 | 5 | 200 |
| Comparative Example 3 | silver nitrate | propylene glycol | lithium chloride | potassium bromide | lithium hydroxide | aluminum nitrate | copolymer A | 0.5257 | 0.0506 | (not reduced) | | |
| Comparative Example 4 | silver nitrate | propylene glycol | lithium chloride | potassium bromide | lithium hydroxide | aluminum nitrate | copolymer A | 0.0789 | 0.6751 | (slight amount of irregular solid matter) | | |
| Comparative Example 5 | silver nitrate | propylene glycol | lithium chloride | potassium bromide | lithium hydroxide | aluminum nitrate | copolymer A | 0.3505 | 0.0032 | (not reduced) | | |
| Comparative Example 6 | silver nitrate | propylene glycol | lithium chloride | potassium bromide | lithium hydroxide | — | copolymer A | 0 | 0.0063 | 160 | 11 | 69 |

*1 copolymer A: copolymer of vinylpyrrolidone and diallyldimethylammonium nitrate copolymer B: copolymer of vinylpyrrolidone and diallyldimethylammonium chloride

The invention claimed is:

1. Silver nanowires comprising Al in an amount of from 100 to 1,000 ppm, the silver nanowires having an average diameter of 50 nm or less and an average length of 10 µm or more, and having coated thereon a copolymer of vinylpyrrolidone and an another monomer.

2. Silver nanowires comprising Al in an amount of from 100 to 1,000 ppm, the silver nanowires having an average diameter of 50 nm or less and an average length of 10 µm or more, and having coated thereon a cationic organic protective agent.

3. Silver nanowires comprising Al in an amount of from 100 to 1,000 ppm, the silver nanowires having an average diameter of 50 nm or less and an average length of 10 µm or more, and having coated thereon a copolymer of vinylpyrrolidone and an additional cationic monomer.

4. Silver nanowires comprising Al in an amount of from 100 to 1,000 ppm, the silver nanowires having an average diameter of 50 nm or less and an average length of 10 µm or more, and having coated thereon a copolymer of vinylpyrrolidone and a diallyldimethylammonium salt monomer.

5. The silver nanowires according to claim 1, wherein assuming that a ratio of the average length (nm) and the average diameter (nm) is referred to as an average aspect ratio, the average aspect ratio is 250 or more.

6. A silver nanowires ink comprising the silver nanowires according to claim 1 in a liquid medium in a content of from 0.05 to 5.0% by mass.

7. A silver nanowires ink comprising the silver nanowires according to claim 2 in a liquid medium in a content of from 0.05 to 5.0% by mass.

8. A silver nanowires ink comprising the silver nanowires according to claim 3 in a liquid medium in a content of from 0.05 to 5.0% by mass.

9. A silver nanowires ink comprising the silver nanowires according to claim 4 in a liquid medium in a content of from 0.05 to 5.0% by mass.

10. The silver nanowires according to claim 2, wherein assuming that a ratio of the average length (nm) and the average diameter (nm) is referred to as an average aspect ratio, the average aspect ratio is 250 or more.

11. The silver nanowires according to claim 3, wherein assuming that a ratio of the average length (nm) and the average diameter (nm) is referred to as an average aspect ratio, the average aspect ratio is 250 or more.

12. The silver nanowires according to claim 4, wherein assuming that a ratio of the average length (nm) and the average diameter (nm) is referred to as an average aspect ratio, the average aspect ratio is 250 or more.

* * * * *